(12) United States Patent
Lam et al.

(10) Patent No.: US 8,663,186 B2
(45) Date of Patent: *Mar. 4, 2014

(54) ABSORBENT ARTICLE WITH IMPROVED TEAR RESISTANCE AND SOFTNESS

(75) Inventors: Joseph Hung Lam, Mason, OH (US); Michael Irwin Lawson, Fairfield, OH (US); Egon Loeffler, Usingen (DE); Douglas Graham, Cincinnati, OH (US); Kaneeta Kimble, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/476,085

(22) Filed: May 21, 2012

(65) Prior Publication Data

US 2012/0238980 A1 Sep. 20, 2012

Related U.S. Application Data

(62) Division of application No. 11/155,981, filed on Jun. 17, 2005, now Pat. No. 8,221,379.

(51) Int. Cl.
*A61F 13/15* (2006.01)

(52) U.S. Cl.
USPC .......................................... 604/391; 604/387

(58) Field of Classification Search
USPC .......................... 604/385.01, 385.03, 385.24, 604/385.27–385.28, 386–391
See application file for complete search history.

(56) References Cited

U.S. PATENT DOCUMENTS

| 5,399,219 | A | * | 3/1995 | Roessler et al. | 156/259 |
| 5,906,008 | A | * | 5/1999 | Heki et al. | 2/400 |
| 6,336,922 | B1 | * | 1/2002 | VanGompel et al. | 604/385.3 |
| 7,217,260 | B2 | * | 5/2007 | Molander et al. | 604/385.24 |

* cited by examiner

*Primary Examiner* — Michele M Kidwell
(74) *Attorney, Agent, or Firm* — Andrew J. Mueller; Laura L. Whitmer

(57) ABSTRACT

A disposable absorbent article may comprise a chassis and an ear. The chassis comprises a liquid permeable topsheet, a backsheet, and an absorbent core disposed between the topsheet and backsheet. The ear comprises an elastomeric material and a first substrate joined to the elastomeric material. The ear has a first void region adjacent the proximal edge of the ear. The ear is joined to the chassis by at least one mechanical bond that engages the elastomeric material.

20 Claims, 9 Drawing Sheets

ABSORBENT ARTICLE WITH IMPROVED TEAR RESISTANCE AND SOFTNESS

CROSS REFERENCE TO RELATED APPLICATIONS

This application is a divisional of U.S. application Ser. No. 11/155,981, filed on Jun. 17, 2005, which is hereby incorporated by reference in its entirety.

FIELD OF THE INVENTION

This invention relates to front and back ear laminates exhibiting improved resistance to tearing for use on absorbent articles such as diapers. The absorbent articles may have improved softness resulting from the material that forms the article's longitudinal edge.

BACKGROUND OF THE INVENTION

It has long been known that absorbent articles such as conventional taped diapers, pull-on diapers, training pants, sanitary napkins, pantiliners, incontinence briefs, and the like, offer the benefit of receiving and containing urine and/or other bodily exudates. To effectively contain exudates, the articles should provide a snug fit around the waist and legs of a wearer. Absorbent articles are known to have a chassis comprising a topsheet, a backsheet, an absorbent core, and barrier and/or gasketing cuffs. Articles such as conventional taped diapers generally include a front and a rear waist section releasably and/or refastenably connected by a fastening system. The fastening system generally comprises an engaging member and a receiving member. The engaging member may be an adhesive tape, a hook bearing tape, or a cohesive tape. The receiving member may be an element or zone on the article that may receive the engaging member such as a polymer film landing zone (viz., for receipt of the adhesive or cohesive tape) or a loop bearing surface (viz., for receipt of the hook bearing tape). The engaging member may be joined to the receiving member thereby interconnecting the rear waist section to the front waist section and thereby forming a waist opening and a pair of leg openings.

Current diaper design frequently includes the use of back ears. Back ears may extend laterally from the longitudinal edge of the rear waist section of the chassis. The engaging member of the fastening system may be attached to the back ear. When the fastening system is engaged, the back ear serves as an interconnecting member between the front waist section and the rear waist section, which together form a waist opening and pair of leg openings. Common back ear construction involves a polymeric material laminated between two substrates. Often back ear construction involves an elastomeric material laminated between two substrates that are supple, soft, and non-irritating to a wearer's skin such as a nonwoven material. Elastomeric films are commonly used since the film provides a degree of stretch to the waist circumference. This stretch allows the diaper to provide a more customized fit. Furthermore, the stretch capability allows the diaper to adjust to the forces exerted by the wearer without causing permanent deformation of the diaper or discomfort for the wearer of the diaper. Elastic back ears are commonly seen in two executions: coterminous and non-coterminous.

Coterminous elastic back ears are back ears where the elastomeric material is substantially coterminous with at least one of the adjoining substrate layers. For example in one commercially available execution, the elastic back ear comprises an elastomeric film between two nonwoven materials. When the back ear is laid flat, the ear has a perimeter. The elastomeric film shares this common perimeter with the nonwoven materials. The problem with coterminous back ears is that elastomeric film is present in locations of the back ear where elastic properties are unnecessary. For example, the back ear may be bonded to the chassis by an adhesive, a pressure bond, or some other bonding technique known in the art. The back ear generally need not exhibit elastic character at points inboard (i.e., closer to the longitudinal centerline of the diaper) of the bond site. As a result, any elastomeric film inboard of the bond site is unnecessary and may represent an added cost to the diaper. Over the course of thousands of diapers produced daily, this added cost without a countervailing consumer benefit can make the diaper unnecessarily expensive. A similar problem may occur where the engaging member is attached to the back ear. The attachment point of the engaging member to the back ear generally prohibits the elastomeric film from stretching. Excess elastomeric film within and outboard of this bond site is unnecessary and may be an added cost.

One way to address the problems present in coterminous elastic back ears is to make the elastomeric material non-coterminous. A non-coterminous back ear has an elastomeric material that does not fully overlap the ear. For example, in one commercially available execution, the back ear comprises an elastomeric film between two nonwoven materials. The back ear has two opposing and substantially parallel edges; one edge being proximate to the rear waist region of the chassis and the other edge being proximate to the engaging member. The elastomeric film has edges that run parallel to but do not share the same edge as the two opposing back ear edges. This results in two void regions in the back ear. The void region is an area of the ear in which no elastomeric film is present. The void region may comprise another substrate such as one or more layers of a nonwoven material. One void region may serve as the bonding location for the back ear to the chassis and the other void region may serve as the bonding location for the engaging member of the fastening system to the back ear. While the non-coterminous back ears improve cost-efficiency of the diaper by reducing unnecessary elastomeric film, these ears can have deficiencies.

One common problem of non-coterminous (as well as coterminous) ears is with regard to joining the ear to the chassis. Back ears are often joined to the chassis by one or more bonding techniques. For example, during manufacture, an adhesive may be applied to the chassis and then the back ear is applied thereto. One problem with the use of adhesive to join the back ear to the chassis relates to over-application. The adhesive is often applied adjacent to the longitudinal edge of the chassis. This proximity to the longitudinal edge can result in adhesive being applied beyond the edge of the chassis, which results in wasted adhesive and increases the manufacturing costs of the article. Furthermore, adhesive overspray can contaminate the process line thereby increasing defects and prompting more frequent line stoppages.

Another problem related to adhesive bonding involves the strength of the adhesive bond. As described above, the back ear generally comprises an elastomeric film between two nonwoven materials. Likewise, the outermost and innermost planar surfaces of the chassis are typically nonwoven materials (i.e., a nonwoven outer cover or a nonwoven topsheet). By adhesively joining the back ear to the chassis, the adhesive is effectively engaging and joining two nonwoven materials (i.e., the nonwoven of the back ear and the nonwoven of the chassis). An adhesive bond between two nonwovens may lack the tensile strength necessary for the back ear, which is subjected to elongating forces when the diaper is applied. To further strengthen the connection of the back ear and the chassis, mechanicals bonds are frequently used.

A variety of mechanical bonding techniques are known in the art. One such technique is pressure bonding, which involves applying high pressure at a bond site to compress the materials to be joined. Particularly with polymeric materials, the pressure may heat the materials enabling them to flow together. Upon cooling, the materials may be fused together and/or may fuse together around the perimeter of the bond site. A plurality of bond sites are typically created and may be arranged in a substantially linear arrangement. While pressure bonding can increase the bond strength between the back ear and the chassis, an unintended consequence of pressure bonding may be weakening of the nonwoven proximate to the bond sites. This weakening is particularly evident when the pressure bonding occurs within the void region of the back ear. Since the pressure bonds may cause the nonwoven material of the void region to flow, the bond sites can serve as perforations in the nonwoven. When a strain is applied to the back ear such as during application of the diaper, the nonwoven is prone to tearing along the bond sites. Such tearing is viewed as highly undesirable since the diaper fails prior to use.

Accordingly, it would be desirable to provide an absorbent article having a front and/or back ear that eliminates the excessive and unnecessary elastomeric material of the coterminous back ears while addressing the bonding issues present in the non-coterminous back ears having a void region.

SUMMARY OF THE INVENTION

The present invention relates to a disposable absorbent article comprising a chassis and an ear. The chassis has a front waist region, a rear waist region, a crotch region between the front waist region and the rear waist region, and a pair of longitudinal edges. The ear has a perimeter, a distal edge, and a proximal edge. The chassis comprises a liquid permeable topsheet, a backsheet, and an absorbent core disposed between the topsheet and backsheet. The ear comprises an elastomeric material and a first substrate joined to the elastomeric material. The ear has a first void region formed adjacent the proximal edge of the ear. The ear extends laterally outward from the longitudinal edge of the chassis in the front waist region or the rear waist region. The ear is joined to the chassis by at least one mechanical bond that engages the elastomeric material.

The present invention is further directed to a disposable absorbent comprising a chassis and an ear. The chassis comprises a liquid permeable topsheet, a backsheet comprising a polymeric film and having a pair of longitudinal edges, an absorbent core disposed between the topsheet and backsheet, and a pair of barrier leg cuffs disposed in at least the crotch region. The barrier leg cuffs each have a proximal edge and a distal edge wherein said distal edge is disposed laterally outboard of the longitudinal edge of the polymeric film. The ear comprises an elastomeric material and a first substrate joined to the elastomeric material. The ear has a first void region formed adjacent the proximal edge of the ear. The ear is joined to the chassis by at least one mechanical bond that engages the elastomeric material.

The present invention is further directed to a disposable absorbent comprising a chassis and an ear. The chassis has a front waist region, a rear waist region, a crotch region between the front waist region and the rear waist region, and a pair of longitudinal edges. The ear has a perimeter, a distal edge, and a proximal edge. The chassis comprises a liquid permeable topsheet having a pair of opposing longitudinal edges; a backsheet comprising an outer cover and a polymeric film disposed between the outer cover and the absorbent core, wherein said outer cover has a pair of longitudinal edges and said polymeric film has a pair of longitudinal edges; an absorbent core disposed between the topsheet and backsheet; and a pair of barrier leg cuffs disposed in at least the crotch region. The barrier leg cuffs each have a proximal edge and a distal edge. The ear comprises an elastomeric material and a first substrate joined to the elastomeric material. The ear has a first void region formed adjacent the proximal edge of the ear. The ear extends laterally outward from the longitudinal edge of the chassis in the front waist region and the rear waist region. The ear is joined to the chassis by at least one mechanical bond. Furthermore, the longitudinal edge of the topsheet, the longitudinal edge of the outer cover, the distal edge of the barrier leg cuff, or any combinations thereof is disposed laterally outboard of the longitudinal edge of the polymeric film.

DETAILED DESCRIPTION OF THE INVENTION

Figure 1:
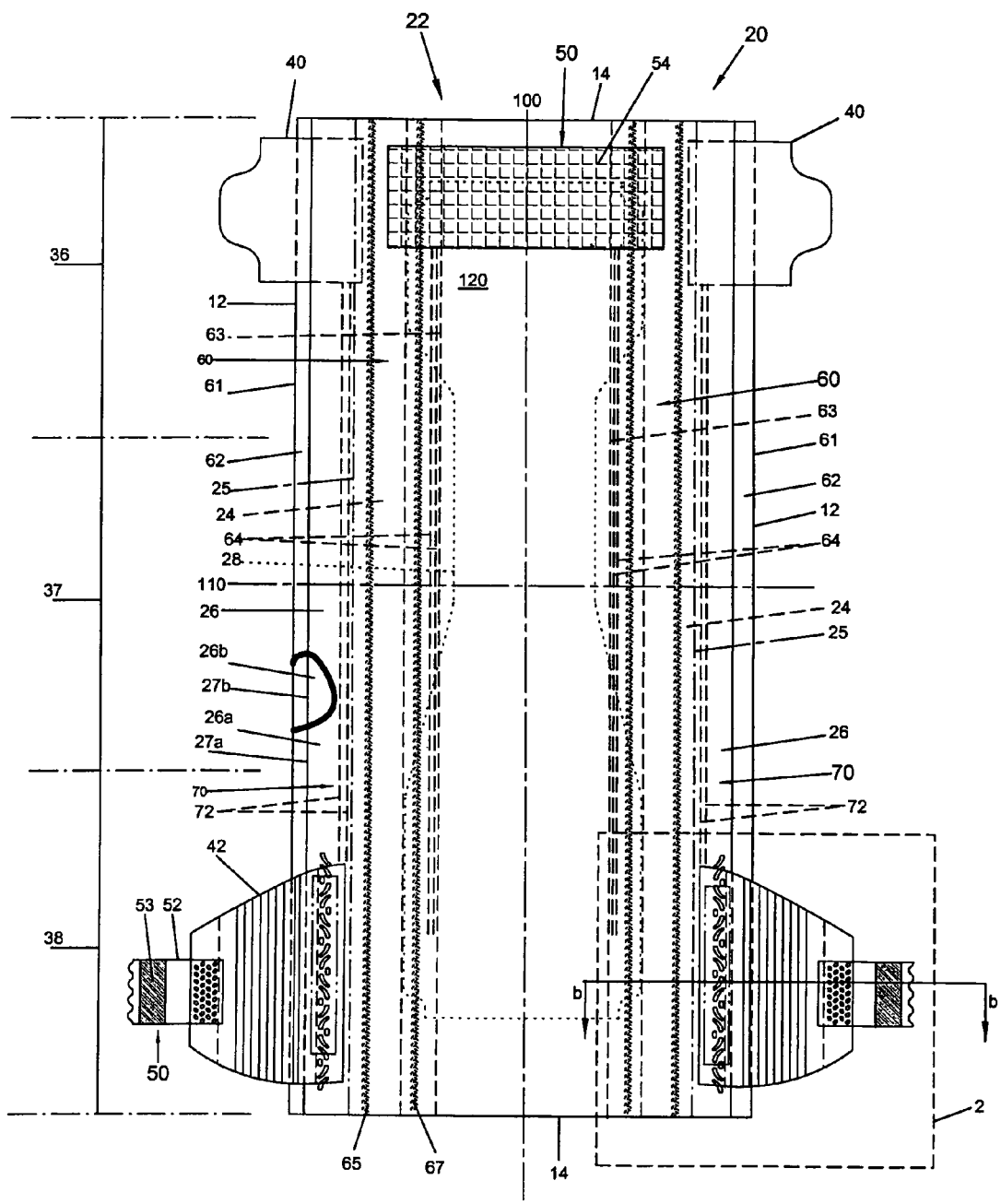
FIG. 1 is a plan view of an exemplary diaper in a flat, uncontracted state.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Mechanical bond" is an attachment between two or more elements, components, regions, or webs and may comprise heat bonds, pressure bonds, ultrasonic bonds, dynamic mechanical bonds, or any other suitable non-adhesive attachment means or combinations of these attachment means as are known in the art.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a preformed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Engage" when used with regard to a first material being joined by a mechanical bond to a second material means that the bond intersects at least a portion of the first material.

"Void region" is an area of an ear where elastomeric material is absent.

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal edges 12 and lateral edges 14. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24 having longitudinal edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features added to form the composite diaper structure. While the topsheet 24, the backsheet 26, and the absorbent core 28 may be assembled in a variety of well-known configurations, preferred diaper configurations are described generally in U.S.

Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A suitable topsheet 24 is available from BBA Fiberweb, Brentwood, Tenn. as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may have longitudinal edges 27a and the inner layer 26b may have longitudinal edges 27b. The outer cover 26a may be made of a soft, non-woven material. The inner layer 26b may be made of a substantially water-impermeable film. The outer cover 26a and an inner layer 26b may be joined together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 depicts a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may have a distal edge 61 and a proximal edge 63 that run substantially parallel to the longitudinal centerline 100. The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap 62 may comprise a nonwoven available from BBA Fiberweb, Brentwood, Tenn. as supplier code 30926. A particularly suitable elastic member 64 is available from Invista, Wichita, Kans. as supplier code T262P. Further description of diapers having barrier cuffs and suitable construction of such barrier cuffs may be found in U.S. Pat. Nos. 4,808,178 and 4,909,803. The elastic member 64 generally spans the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the proximal edge 63 of the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and back ears 42. The front and/or back ears 40, 42 may be unitary elements of the diaper 20 (i.e., they are not separately manipulative elements secured to the diaper 20, but rather are formed from and are extensions of one or more of the various layers of the diaper). In certain embodiments, the front and/or back ears 40, 42 may be discrete elements that are joined to the chassis 22, as shown in FIG. 1. Discrete front and/or back ears 40, 42 may be joined to the chassis 22 by any bonding method known in the art such as adhesive bonding, pressure bonding, heat bonding, and the like. In other embodiments, the front and/or back ears 40, 42 may comprise a discrete element joined to the chassis 22 with the chassis 22 having a layer, element, or substrate that extends over the front and/or back ear 40, 42. The front ears 40 and back ears 42 may be extensible, inextensible, elastic, or inelastic. The front ears 40 and back ears 42 may be formed from nonwoven webs, woven webs, knitted fabrics, polymeric and elastomeric films, apertured films, sponges, foams, scrims, and combinations and laminates thereof. In certain embodiments the front ears 40 and back ears 42 may be formed of a nonwoven/elastomeric material laminate or a nonwoven/elastomeric material/nonwoven laminate. A suitable elastic back ear 42 may be a laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). While the following embodiments are directed to back ear 42 design and construction, these embodiments are equally applicable to front ear 40 design and construction. It should be recognized that any combination of the following embodiments may be used for the back ear 42 and/or the front ear 40.

Figure 2A:
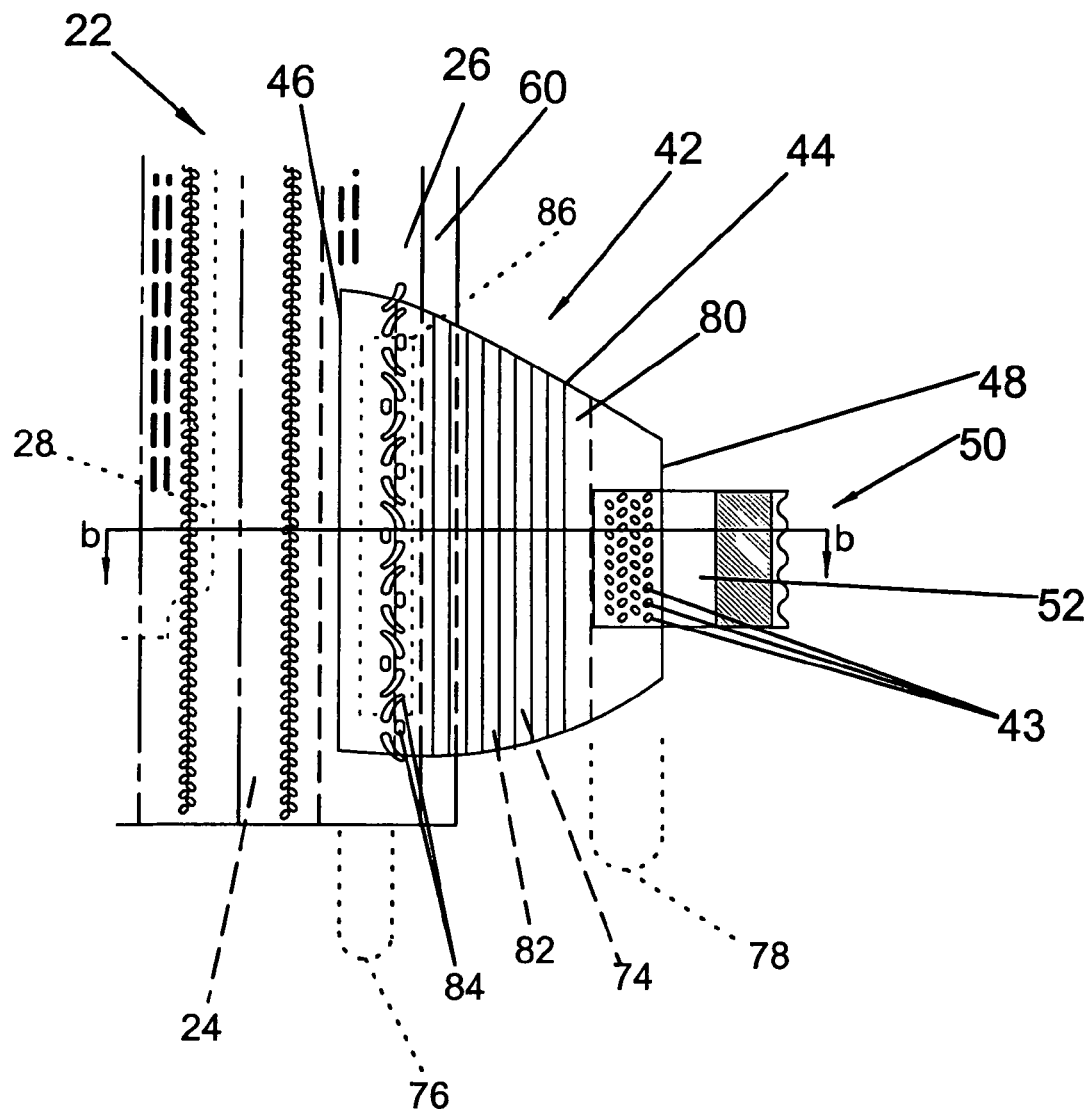
FIG. 2A is a top view of the boxed portion 2 of FIG. 1 enlarged to show structural detail of a suitable embodiment of the present invention.
Figure 2B:
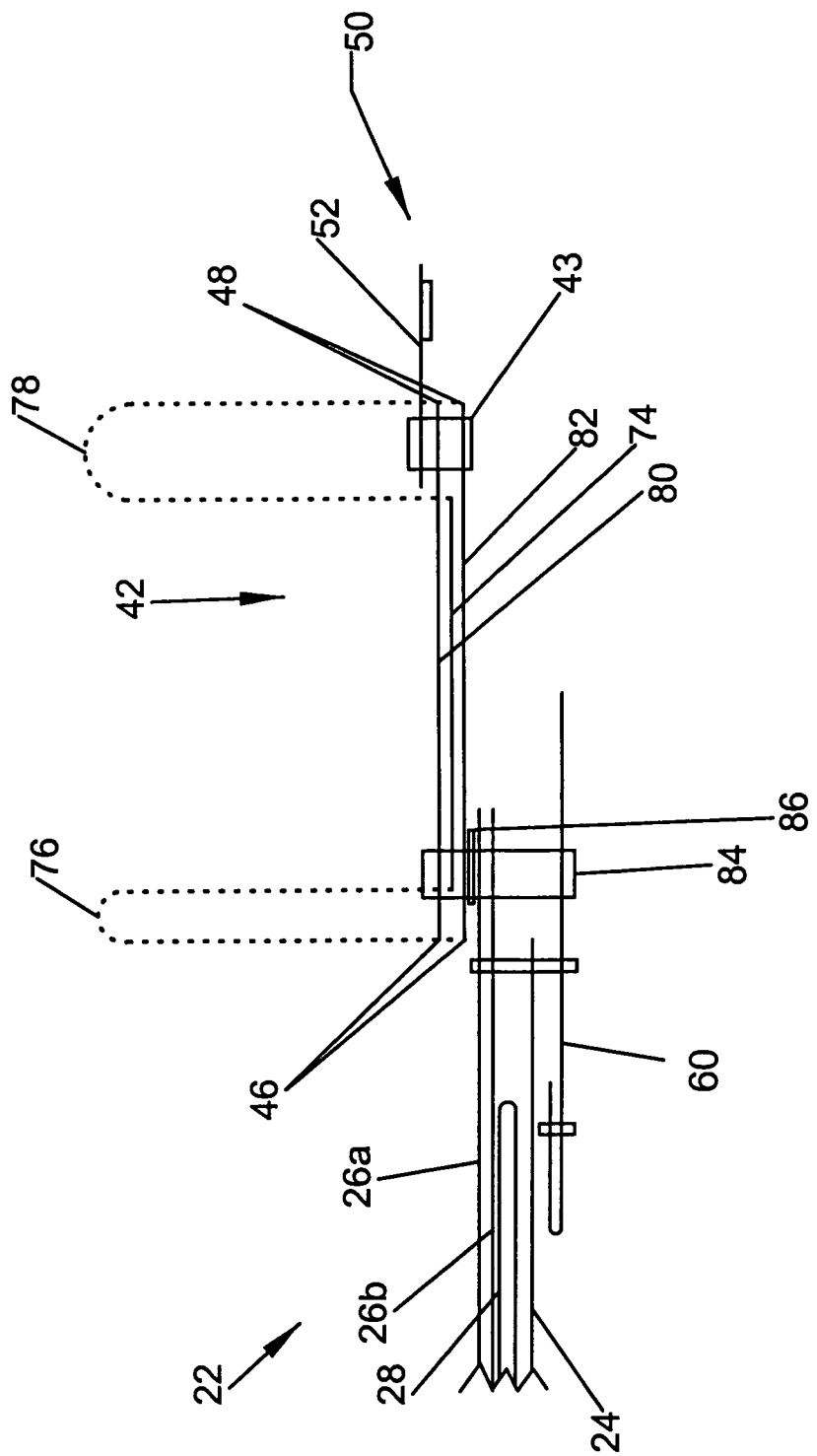
FIG. 2B is a cross-sectional view taken through the sectional line b-b as shown in FIG. 2A.
Figure 3A:
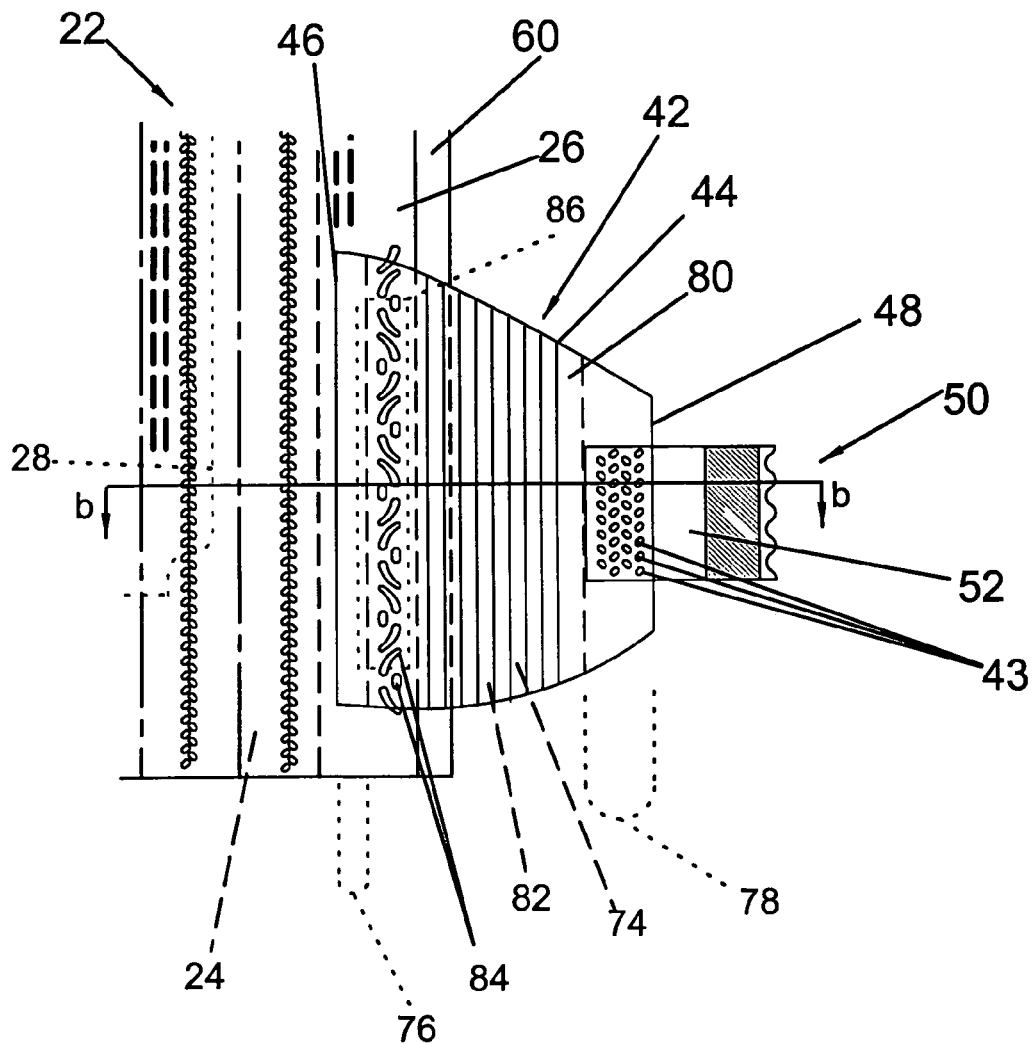
FIG. 3A is a top view of another suitable embodiment of the present invention.
Figure 3B:
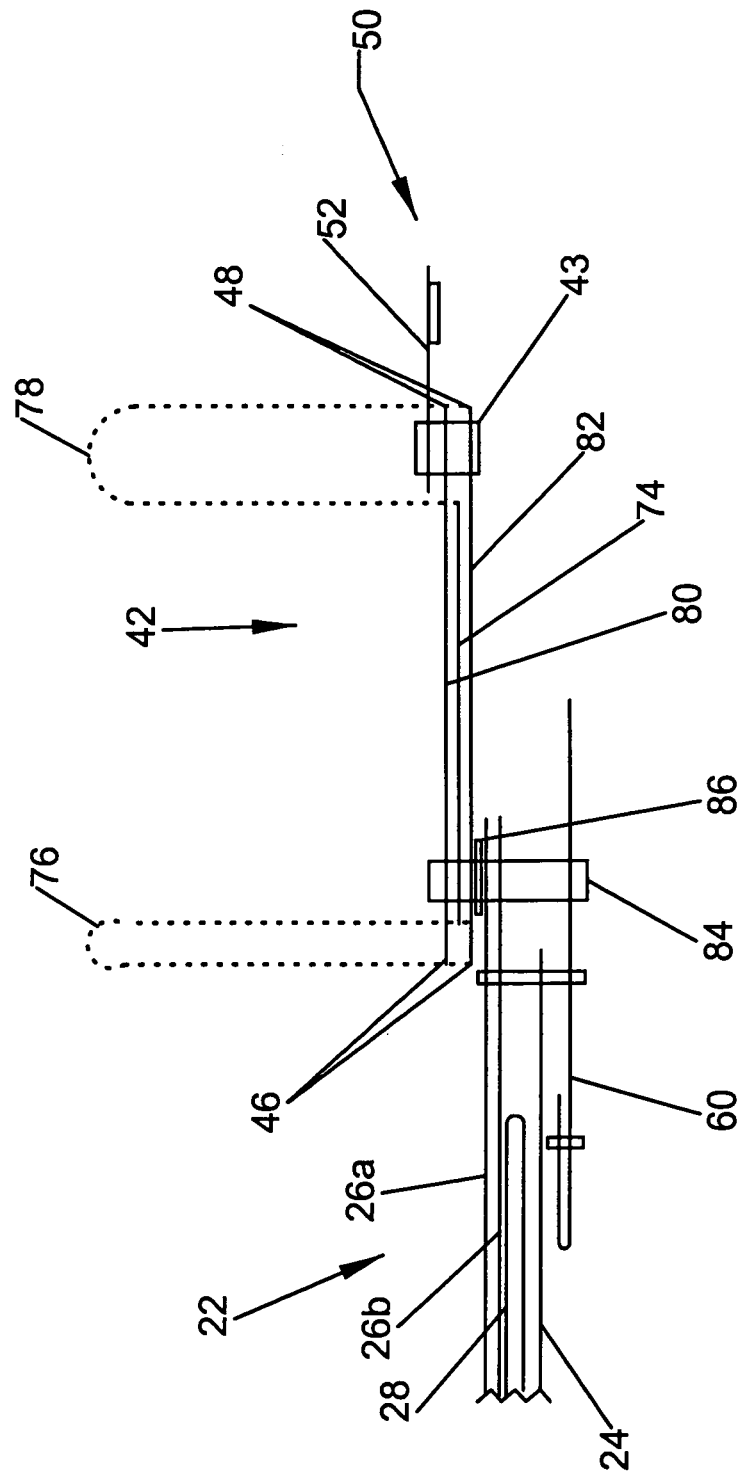
FIG. 3B is a cross-sectional view taken through the sectional line b-b as shown in FIG. 3A.
Figure 4A:
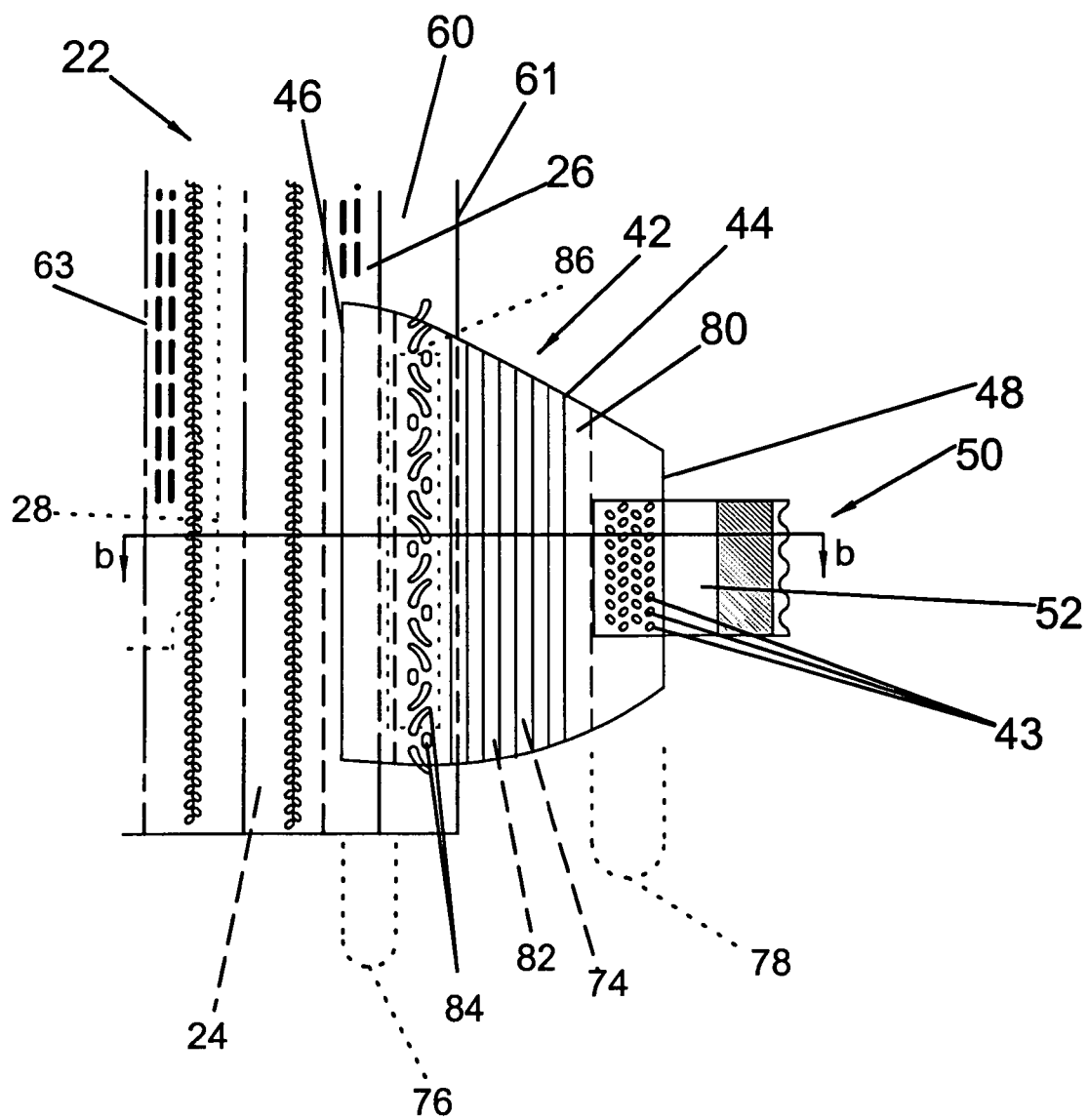
FIG. 4A is a top view of another suitable embodiment of the present invention.

While FIG. 1 provides a general illustration of diaper 20, particular chassis 22 and back ear 42 embodiments are illustrated in FIGS. 2A-B, 3A-B, 4A-B, 5, and 6. FIGS. 2A, 3A, and 4A are enlarged top views of the structures within the boxed portion 2 of FIG. 1. FIGS. 2B, 3B, 4B, 5, and 6 are cross-sectional views of the structures through sectional line b-b of FIG. 1 (sectional line b-b is also shown in FIGS. 2A, 3A, and 4A). Referring now to FIGS. 2A-B, a back ear 42 is shown having a perimeter 44, a proximal edge 46, and a distal edge 48. The back ear 42 may comprise an elastomeric material 74 disposed between a first substrate 80 and a second substrate 82. In alternate embodiments, the back ear 42 may comprise the elastomeric material 74 laminated to a single substrate or to multiple substrates. The first and second substrate 80, 82 have a perimeter that may be coterminous with the back ear perimeter 44. The first and second substrate 80, 82 may be a nonwoven web, a woven web, a knitted fabric, a polymeric film, an elastomeric film, an apertured film, a sponge, a foam, a scrim, and combinations and laminates thereof. In certain embodiments, the first and second substrate 80, 82 may be a nonwoven web such as a spunbond web, a meltblown web, a spunbond-meltblown web, a spunbond-meltblown-spunbond web, a carded web, an airlaid web, laminates thereof, and derivatives thereof.

The elastomeric material 74 may occupy an area smaller than the area defined by the perimeter 44 of the back ear 42 thereby creating a first void region 76. A void region is an area of the back ear 42 where the elastomeric material 74 is absent. FIG. 2A-B illustrates that first void region 76 as being adjacent the proximal edge 46 of the back ear 42. In other suitable embodiments, additional void regions may exist. As further illustrated in FIG. 2A-B, a second void region 78 may be formed adjacent the distal edge 48 of the back ear 42. The elastomeric material 74 or substrates 80, 82 may be sized to provide the first void region 76, the second void region 78, and/or other void regions.

FIGS. 2A-B show the engaging member 52 (which is a portion of the fastening system 50) joined to the back ear 42 by a plurality of bonds 43. The bonds 43 may be formed by any bonding method known in the art including adhesive bond, ultrasonic bonds, compression bonds, thermal bonds, and combinations thereof. The bonds 43 may engage the second void region 78, the elastomeric material 74, or both. FIGS. 2A-B show the bonds 43 engaging the second void region 78.

The back ear 42 may be joined to the chassis 22 by one or more mechanical bonds 84. As shown in FIG. 2A, a plurality of mechanical bonds 84 may be used. The mechanical bond 84 and the elastomeric material 74 may be disposed such that the mechanical bond 84 engages a portion of the elastomeric material 74 and the first void region 76. In this embodiment, at least one of the discrete bonds engages the elastomeric material 74 and the first void region 76. While the back ear 42 is shown in FIGS. 2A-B as being disposed on the garment-facing surface of the chassis 22, the back ear 42 may be disposed on the body-facing surface of the chassis 22 or may be disposed between elements that form the chassis 22 (e.g., the back ear may be disposed between the backsheet 26 and the barrier cuff 60). Optionally, the back ear 42 may also be joined to the chassis 22 by use of an adhesive area 86 in conjunction with the mechanical bond 84. The adhesive area 86 may be positioned such that a portion of the area 86 engages the overlapping regions between the back ear 42 and the chassis 22. It may be desirable for the adhesive area 86 to overlap a portion of the mechanical bond. Suitable adhesives (such as marketed by Bostik Findley, Inc., Wauwatosa, Wis., as Findley Adhesive 581) and application techniques are well known in the art.

FIGS. 3A-B illustrates another embodiment for joining the back ear 42 to the chassis 22. FIG. 3A is a top view of the back ear 42 and a portion of the chassis 22 enlarged to show structural detail. FIG. 3B is a cross-sectional view through the sectional line b-b as shown in FIG. 3A. The back ear 42 may be joined to the chassis 22 by one or more mechanical bonds 84. As shown in FIG. 3A, a plurality of mechanical bonds 84 may be used. FIGS. 3A-B show that the mechanical bonds 84 and the elastomeric material 74 may be disposed such that the mechanical bonds 84 engage the elastomeric material 74 without engaging the first void region 76. Optionally, the back ear 42 may also be joined to the chassis 22 by use of an adhesive area 86 in conjunction with the mechanical bond 84.

FIGS. 3A-B show the engaging member 52 (which is a portion of the fastening system 50) joined to the back ear 42 by a plurality of bonds 43. The bonds 43 may be formed by any bonding method known in the art including adhesive bond, ultrasonic bonds, compression bonds, thermal bonds, and combinations thereof. The bonds 43 may engage the second void region 78, the elastomeric material 74, or both. FIGS. 3A-B show the bonds 43 engaging the second void region 78.

Figure 4B:
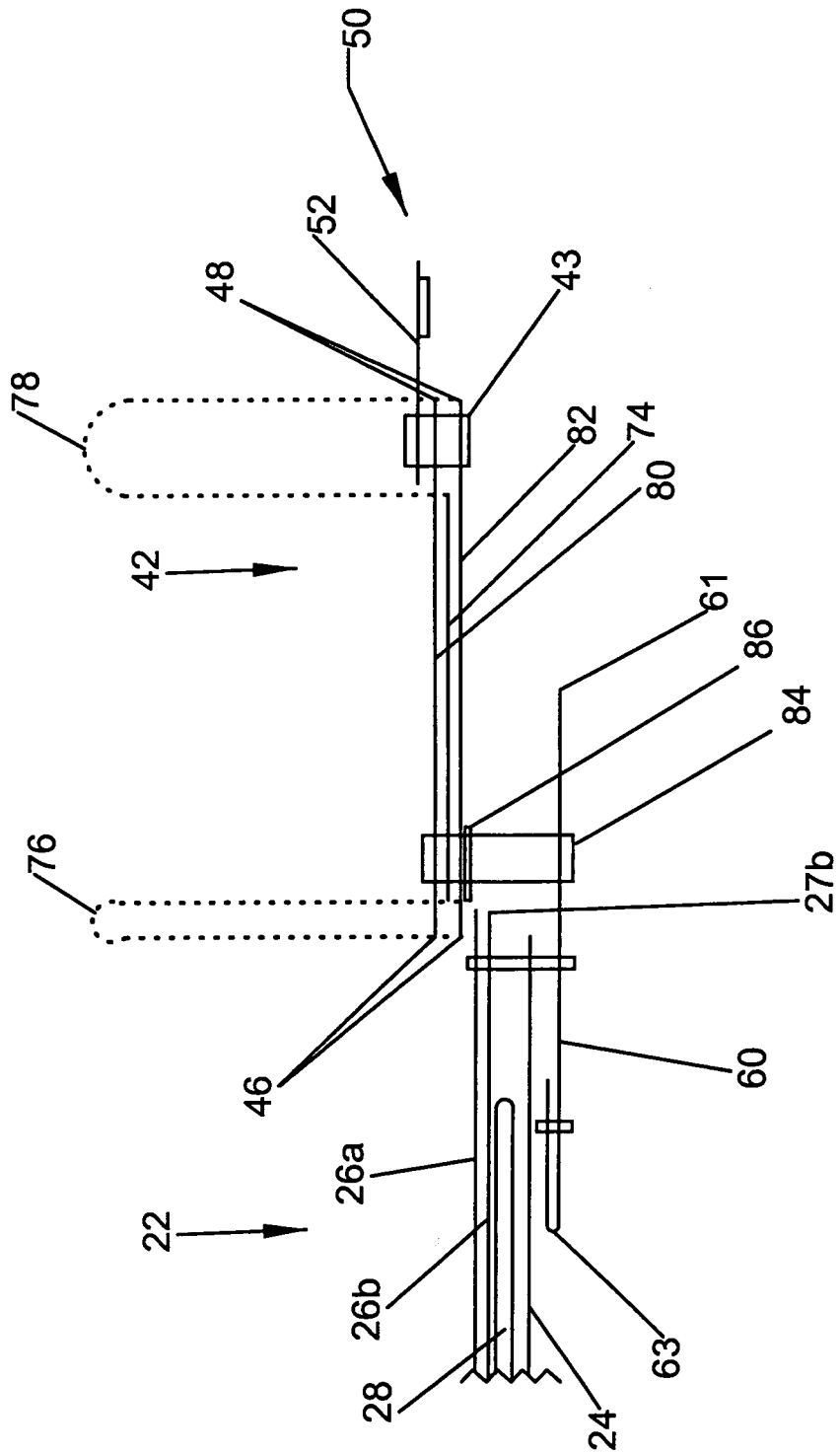
FIG. 4B is a cross-sectional view taken through the sectional line b-b as shown in FIG. 4A.

The embodiments illustrated in FIGS. 2B-3B show a plurality of mechanical bonds 84 engaging the inner layer 26b of the backsheet 26. As disclosed above, the inner layer 26b may be made of a substantially water-impermeable film. In other embodiments, as shown in FIGS. 4A-B, it may be desirable that the mechanical bond 84 not engage the inner layer 26b. FIG. 4A is a top view of the back ear 42 and a portion of the chassis 22 enlarged to show structural detail. FIG. 4B is a cross-sectional view of the boxed portion 2 taken along the sectional line b-b as shown in FIG. 4A. As shown in FIG. 4B, the mechanical bond 84 engages the portion of the barrier cuff 60 that lies outboard of the longitudinal edge 27b of the inner layer 26b. The mechanical bonds 84 and, optionally, the adhesive area 86 may vary in placement and in dimension. However, the distal edge 61 of the barrier cuff 60 desirably lies outboard of the longitudinal edge 27b of the inner layer 26b a distance sufficient so that the mechanical bond 84 can be formed without engaging the inner layer 26b. In certain embodiments, the distal edge 61 of the barrier cuff 60 may extend at least about 7.5 mm beyond the longitudinal edge 27b of the inner layer 26b. Alternatively, the distal edge 61 of the barrier cuff 60 extends at least about 10 mm, about 12.5 mm, about 15 mm, about 17.5 mm, or about 20 mm beyond the longitudinal edge 27b of the inner layer 26b.

In certain embodiments, the distal edge 61 of the barrier cuff 60 may extend beyond the longitudinal edge 27b of the inner layer 26b over substantially the entire longitudinal length of the chassis 22. In other embodiments, the distal edge 61 of the barrier cuff 60 may extend beyond the longitudinal edge 27b of the inner layer 26b in at least the front waist region 36, the rear waist region 38, and/or the crotch region 37 of the chassis 22. In a particularly suitable embodiment, the distal edge 61 of the barrier cuff 60 may extend beyond the longitudinal edge 27b of the inner layer 26b in at least the crotch region 37. It is believed that extending the distal edge 61 of the barrier cuff 60 beyond the longitudinal edge 27b of the inner layer 26b provides a softer substrate (e.g., typically a nonwoven) in close proximity to a wearer's skin as opposed to the relatively stiff and rough inner layer 26b, which is often a polymeric film. The extension of the barrier cuff 60 beyond the inner layer 26b is particularly beneficial in the crotch region 37 of the diaper 20 where the longitudinal edge of the diaper 20 is gathered and held in close proximity to the wearer's skin due, in part, to the elastic members 72, 64 of the gasketing leg cuff 70 and the barrier leg cuff 60, respectively (as seen in FIG. 4A). Furthermore, extension of the barrier cuff 60 beyond the inner layer 26b aids in reducing the over-application of the optional adhesive.

Figure 5:
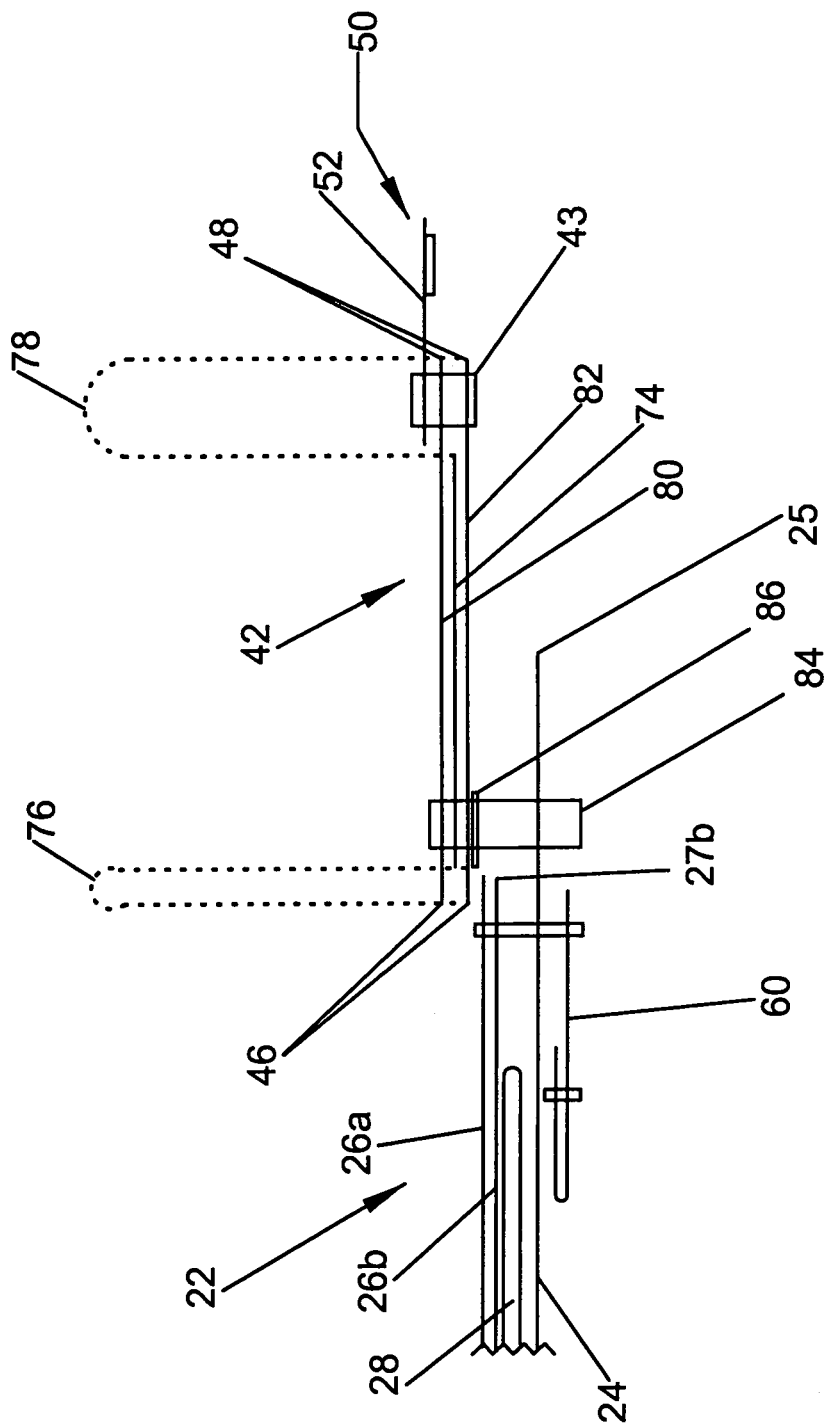
FIG. 5 is a cross-sectional view taken along sectional line b-b of FIG. 1 showing another suitable embodiment of the present invention.
Figure 6:
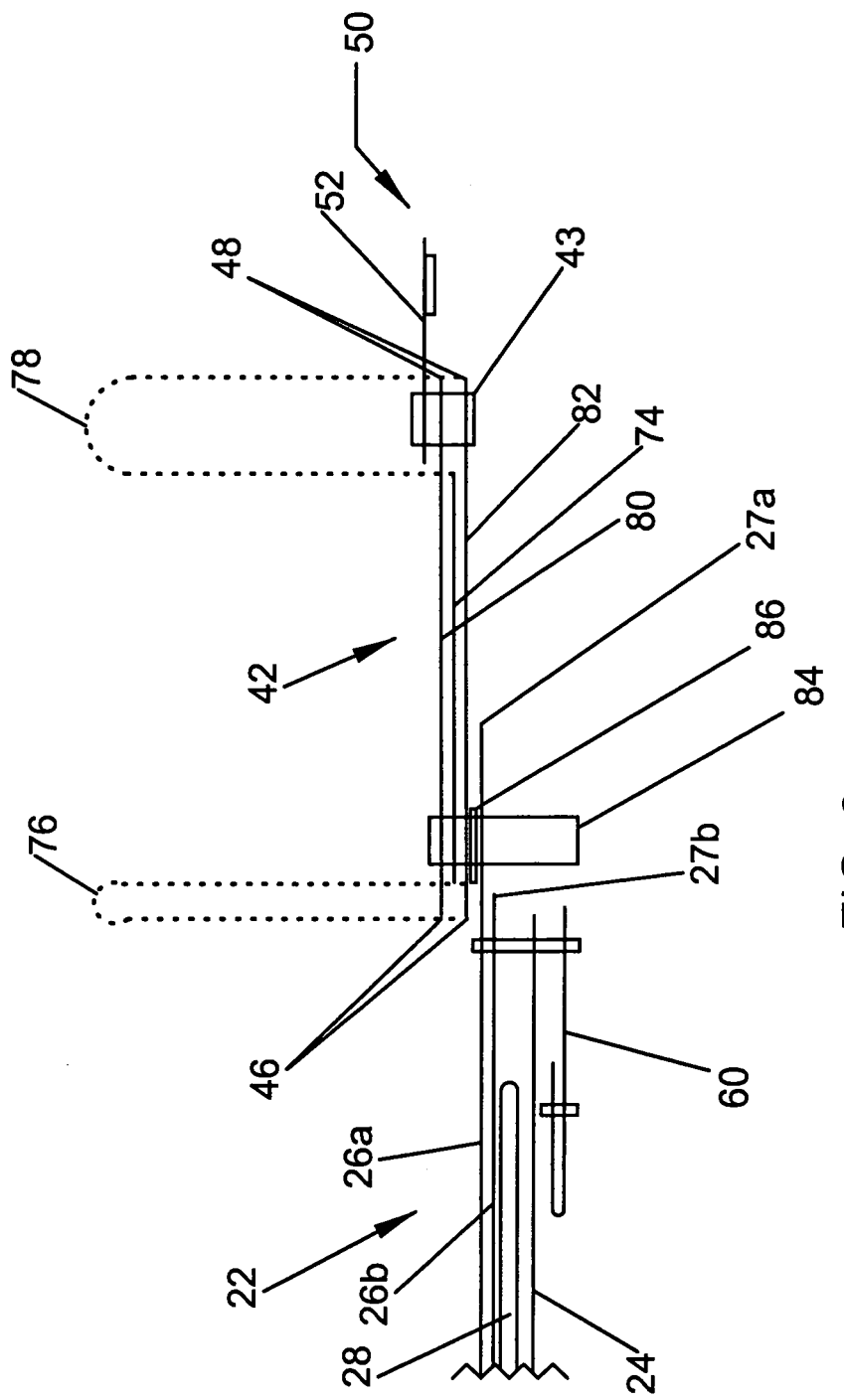
FIG. 6 is a cross-sectional view taken along sectional line b-b of FIG. 1 showing another suitable embodiment of the present invention.

In other suitable embodiments, the mechanical bond 84 and, optionally, the adhesive area 86 may engage other elements of the diaper 20 that extend outboard of the longitudinal edge 27b of the inner layer 26b. For example, FIG. 5 shows a cross-sectional view of the back ear 42 and a portion of the chassis 22 taken along sectional line b-b of FIG. 1, the mechanical bond 84 may engage a portion of the topsheet 24 that extends beyond the longitudinal edge 27b of the inner layer 26b. In another embodiment, as shown in the cross-sectional view of the back ear 42 and a portion of the chassis 22 in FIG. 6 taken along sectional line b-b of FIG. 1, the mechanical bond 84 may engage a portion of the outer cover 26a that extends beyond the longitudinal edge 27b of the inner layer 26b. As with the barrier cuff 60, the longitudinal edge 25 of the topsheet 24 or the longitudinal edge 27a of the outer cover 26a desirably lies outboard of the longitudinal edge 27b of the inner layer 26b a distance sufficient to create the mechanical bond 84 without engaging the inner layer 26b. In certain embodiments, longitudinal edge 25 of the topsheet 24 or the longitudinal edge 27a outer cover 26a the extends at least about 7.5 mm, about 10 mm, about 12.5 mm, about 15 mm, about 17.5 mm, or about 20 mm beyond the longitudinal edge of the inner layer 26b. Furthermore, the topsheet 24 or the outer cover 26a may extend beyond the longitudinal edge 27b of the inner layer 26b over substantially the entire longitudinal length of the chassis 22. In other embodiments, the topsheet 24 or the outer cover 26a may extend beyond the longitudinal edge 27b of the inner layer 26b in at least the front waist region 36, the rear waist region 38, and/or the crotch region 37 of the chassis 22. In a particularly suitable embodiment, the topsheet 24 or the outer cover 26a may extend beyond the longitudinal edge 27b of the inner layer 26b in at least the crotch region 37.

In certain embodiments, any combination of the barrier cuff 60, the topsheet 24, and the outer cover 26a may extend beyond the longitudinal edge 27b of the inner layer 26b. The distal edge 61 of the barrier cuff 60, the longitudinal edge 25 of the topsheet 24, and the longitudinal edge 27a of the outer cover 26a may be coterminous or non-coterminous. Furthermore, the diaper 20 of the present invention may have the mechanical bond 84 engaging the inner layer 26b (as shown in FIGS. 2A-B and 3A-B) and may also have any combination of the barrier cuff 60, the topsheet 24, and the outer cover 26a extending beyond the longitudinal edge of the inner layer 26b.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising
   a) a chassis having a front waist region, a rear waist region, a crotch region between the front waist region and the rear waist region, and a pair of longitudinal edges, said chassis comprising:
      i) a liquid permeable topsheet,
      ii) a backsheet, and
      iii) an absorbent core disposed between the topsheet and backsheet; and
   b) an ear having a perimeter, a distal edge, and a proximal edge; said ear comprising
      i) an elastomeric material and
      ii) a first substrate joined to the elastomeric material
      wherein the ear has a first void region adjacent the proximal edge of the ear, wherein elastomeric material, but not first substrate, is absent from the first void region,
      wherein at least a portion of said ear extends laterally outward from one of the longitudinal edges of the chassis in the front waist region or the rear waist region, and
      wherein the ear is joined to the chassis by at least one mechanical bond that engages the elastomeric material.

2. The disposable absorbent article of claim 1 wherein the mechanical bond is selected from the group consisting of heat bonds, pressure bonds, ultrasonic bonds, dynamic mechanical bonds, and combinations thereof.

3. The disposable absorbent article of claim 1 wherein the ear further comprises a second substrate joined to the elastomeric material such that the elastomeric material is disposed between the first substrate and the second substrate.

4. The disposable absorbent article of claim 1 wherein the mechanical bond engages the first void region.

5. The disposable absorbent article of claim 1 wherein the mechanical bond engages the elastomeric material without engaging the first void region.

6. The disposable absorbent article of claim 1 wherein the backsheet comprises an outer cover and a polymeric film disposed between the outer cover and the absorbent core, wherein the mechanical bond engages the polymeric film.

7. The disposable absorbent article of claim 1 wherein is the ear is joined to the chassis by an adhesive.

8. The disposable absorbent article of claim 1 wherein the first substrate is selected from the group consisting of nonwoven webs, woven webs, knitted fabrics, films, apertured films, sponges, foams, scrims, and any combinations and laminates thereof.

9. The disposable absorbent article of claim 1 wherein the first substrate is selected from the group consisting of a spunbond web, a meltblown web, spunbond-meltblown web, a spunbond-meltblown-spunbond web, a carded web, an airlaid web, laminates thereof, and derivatives thereof.

10. The disposable absorbent article of claim 1 wherein the ear has a second void region formed adjacent the distal edge of the ear.

11. The disposable absorbent article of claim 10 wherein the absorbent article further comprises a fastening system, wherein said fastening system comprises an engaging member joined to the distal edge of the car by at least one secondary mechanical bond that engages the elastomeric material.

12. The disposable absorbent article of claim 1 wherein the elastomeric material is in the form of an elastomeric film, an elastomeric scrim, an elastomeric nonwoven; or combinations thereof.

13. A disposable absorbent article comprising
    a) a chassis having a front waist region, a rear waist region, a crotch region between the front waist region and the rear waist region, and a pair of longitudinal edges, said chassis comprising
       i) a liquid permeable topsheet,
       ii) a backsheet comprising a polymeric film and having a pair of longitudinal edges,
       iii) an absorbent core disposed between the topsheet and backsheet, and
       iv) a pair of barrier leg cuffs disposed in at least the crotch region, said barrier leg cuffs each having a proximal edge and a distal edge wherein said distal edge is disposed laterally outboard of the longitudinal edge of the polymeric film; and
    b) an ear having a perimeter, a distal edge, and a proximal edge; said ear comprising
       i) an elastomeric material and
       ii) a first substrate joined to the elastomeric material
       wherein the ear has a first void region adjacent the proximal edge of the ear, wherein elastomeric material, but not first substrate, is absent from the first void region,
       wherein at least a portion of said ear extends laterally outward from the longitudinal edge of the chassis in the front waist region or the rear waist region, and
       wherein the ear is joined to the chassis by at least one mechanical bond that engages the elastomeric material.

14. The disposable absorbent article of claim 13 wherein the distal edge of the barrier leg cuff is disposed laterally outboard of the longitudinal edge of the polymeric film by at least about 7.5 mm.

15. The disposable absorbent article of claim 13 wherein the distal edge of the barrier leg cuff is disposed laterally outboard of the longitudinal edge of the polymeric film in the crotch region.

16. The disposable absorbent article of claim 13 wherein the backsheet further comprises a nonwoven outer cover having a pair of longitudinal edges, wherein said nonwoven outer cover is disposed such that the polymeric film is between the nonwoven outer cover and the absorbent core.

17. The disposable absorbent article of claim 16 wherein the longitudinal edges of the nonwoven outer cover are coterminous with the distal edge of the barrier leg cuff.

18. The disposable absorbent article of claim 13 wherein the mechanical bond engages the barrier leg cuff laterally outboard of the longitudinal edge of the polymeric film.

19. A disposable absorbent article comprising
a) a chassis having a front waist region, a rear waist region, a crotch region between the front waist region and the rear waist region, and a pair of longitudinal edges, said chassis comprising:
  i) a liquid permeable topsheet having a pair of opposing longitudinal edges,
  ii) a backsheet comprising an outer cover and a polymeric film disposed between the outer cover and the absorbent core, wherein said outer cover has a pair of longitudinal edges and said polymeric film has a pair of longitudinal edges,
  iii) an absorbent core disposed between the topsheet and backsheet, and
  iv) a pair of barrier leg cuffs disposed in at least the crotch region, said barrier leg cuffs each having a proximal edge and a distal edge; and
b) an ear having a perimeter, a distal edge, and a proximal edge; said ear comprising
  i) an elastomeric material and
  ii) a first substrate joined to the elastomeric material
  wherein the ear has a first void region adjacent the proximal edge of the ear, wherein elastomeric material, but not first substrate, is absent from the first void region,
  wherein said ear extends laterally outward from the longitudinal edge of the chassis in the front waist region and the rear waist region,
  wherein at least a portion of said ear is joined to the chassis by at least one mechanical bond, and
  wherein the longitudinal edge of the topsheet, the longitudinal edge of the outer cover, the distal edge of the barrier leg cuff, or combinations thereof is disposed laterally outboard of the longitudinal edge of the polymeric film by at least about 7.5 mm.

20. The disposable absorbent article of claim 19 wherein the mechanical bond engages the elastomeric material.

* * * * *

UNITED STATES PATENT AND TRADEMARK OFFICE
CERTIFICATE OF CORRECTION

| | | |
|---|---|---|
| PATENT NO. | : 8,663,186 B2 | Page 1 of 1 |
| APPLICATION NO. | : 13/476085 | |
| DATED | : March 4, 2014 | |
| INVENTOR(S) | : Joseph Hung Lam et al. | |

It is certified that error appears in the above-identified patent and that said Letters Patent is hereby corrected as shown below:

In the Claims

Column 14, Line 29 – Replace "car" with -- ear --

Signed and Sealed this
Twenty-seventh Day of May, 2014

Michelle K. Lee
*Deputy Director of the United States Patent and Trademark Office*